(12) United States Patent
Hurwitz

(10) Patent No.: US 7,842,020 B2
(45) Date of Patent: Nov. 30, 2010

(54) DOUBLE DIAPER SYSTEM

(75) Inventor: Marni Markell Hurwitz, Far Hills, NJ (US)

(73) Assignee: I Did It, Inc., Far Hills, NJ (US)

( * ) Notice: Subject to any disclaimer, the term of this patent is extended or adjusted under 35 U.S.C. 154(b) by 766 days.

(21) Appl. No.: 11/601,353

(22) Filed: Nov. 17, 2006

(65) Prior Publication Data
US 2008/0119812 A1    May 22, 2008

(51) Int. Cl.
A61F 13/76  (2006.01)
A61F 13/66  (2006.01)
A61F 13/82  (2006.01)
A61F 13/505 (2006.01)

(52) U.S. Cl. .......................... 604/385.14; 604/385.13; 604/387; 604/398; 604/368; 604/370; 604/371; 604/374; 604/378

(58) Field of Classification Search ............ 604/385.01, 604/385.03–385.04, 385.13–385.14, 389–391, 604/397–398, 368, 370–371, 374, 378, 387
See application file for complete search history.

(56) References Cited

U.S. PATENT DOCUMENTS

| | | | | |
|---|---|---|---|---|
| 3,367,334 A | * | 2/1968 | Testa ........................... | 604/370 |
| 3,981,306 A | * | 9/1976 | Krusko ........................ | 604/365 |
| 4,022,210 A | | 5/1977 | Glassman .................... | 604/394 |
| 4,062,817 A | | 12/1977 | Westerman ............... | 525/330.2 |
| 4,076,663 A | | 2/1978 | Masuda et al. ............ | 525/54.31 |
| 4,265,245 A | | 5/1981 | Glassman .................... | 604/365 |
| 4,286,082 A | | 8/1981 | Tsubakimoto et al. ...... | 526/240 |
| 4,333,461 A | | 6/1982 | Muller ........................ | 604/368 |
| 4,340,706 A | | 7/1982 | Obayashi et al. ............ | 526/207 |
| 4,360,021 A | | 11/1982 | Stima ......................... | 604/365 |
| 4,699,619 A | | 10/1987 | Bernardin ................... | 604/378 |
| 4,798,603 A | | 1/1989 | Meyer et al. ................ | 604/378 |
| 4,834,735 A | | 5/1989 | Alemany et al. ............ | 604/368 |
| 4,838,885 A | | 6/1989 | Bernardin .............. | 604/385.22 |
| 4,892,598 A | | 1/1990 | Stevens et al. ............... | 156/91 |
| 5,147,343 A | | 9/1992 | Kellenberger ............... | 604/368 |
| 5,149,335 A | | 9/1992 | Kellenberger et al. ....... | 604/372 |
| 5,217,447 A | | 6/1993 | Gagnon ...................... | 604/397 |
| 5,342,340 A | | 8/1994 | Kichefski et al. ....... | 604/385.25 |
| 5,720,738 A | | 2/1998 | Clark .................... | 604/385.01 |
| 5,725,518 A | | 3/1998 | Coates ........................ | 604/391 |
| 6,108,823 A | * | 8/2000 | Danes ........................... | 2/403 |

(Continued)

*Primary Examiner*—Karin M Reichle
(74) *Attorney, Agent, or Firm*—Ernest D. Buff & Associates, LLC; Ernest D. Buff; Margaret A. La Croix (57) ABSTRACT

A double diaper package includes adhesively attached, similarly sized inner and outer diapers. Each of the diapers has a liquid permeable skin contacting net and a liquid impermeable polymeric back sheet edge bonded to each other so as to surround and encase a super-absorber in a fibrous matrix. The inner diaper has an adhesive coated edge flap of the liquid impermeable sheet extending from the edge bond. This edge flap secures the outer diaper to the inner diaper, forming a double diaper package that is attached to the baby using waist-securing tabs connected to the inner diaper. When soiled, the inner diaper is pulled away by releasing the waist-securing tabs and the adhesive edge flap attachment. The fresh, clean, outer diaper is attached using the waist-securing tabs of the outer diaper. The inner soiled diaper is then discarded.

8 Claims, 4 Drawing Sheets

U.S. PATENT DOCUMENTS

| | | | |
|---|---|---|---|
| 6,114,597 A | 9/2000 | Romare | 604/378 |
| 6,193,702 B1 | 2/2001 | Spencer | 604/385.03 |
| 6,336,923 B1 | 1/2002 | Fujioka et al. | 604/394 |
| 6,793,649 B1 * | 9/2004 | Fujioka et al. | 604/385.05 |
| 7,090,665 B2 | 8/2006 | Ohashi et al. | 604/385.14 |
| 2002/0143316 A1 * | 10/2002 | Sherrod et al. | 604/385.101 |
| 2005/0215968 A1 * | 9/2005 | Henderson | 604/385.14 |

* cited by examiner

DOUBLE DIAPER SYSTEM

BACKGROUND OF THE INVENTION

1. Field of the Invention

The present invention relates to diapers; and, more particularly, to a diaper system wherein a plurality of diapers comprising an inner diaper and an outer diaper are attached to each other so that the soiled inner diaper may be readily removed to thereby expose a fresh outer diaper.

2. Description of the Prior Art

A number of prior art patents relate to the use of multiple layered diapers. These multiple layers allow improved absorption of liquids and do not constitute separate diapers. Liquid retaining capacity is oftentimes absent, since the strength and size these multiple layered diapers is generally inadequate to meet the required level of urine absorption.

U.S. Pat. No. 4,022,210 to Glassman discloses a disposable diaper having a supplemental insert. This disposable diaper has a removable laminated supplemental insert formed with a pull tab to permit its separation from the diaper. Both the diaper and insert have means to insure spreading of any moisture deposited thereon. The insert also includes means to initially hold the margins of the diaper folded. Due to the small size of the insert, the liquid discharged by the baby tends to overwhelm the liquid capturing capacity of the insert. The insert does not contain moisture absorption superabsorbers and therefore has only limited fluid absorption capability. The underlying diaper may therefore be soiled and removal of the insert does not guarantee a fresh diaper underneath.

U.S. Pat. No. 4,265,245 to Glassman discloses a double-duty diaper. This diaper comprises a main diaper having an outer layer of water impervious material and a body contacting inner layer of moisture absorbent material, such as starch. It also includes a removable insert strip arranged on the body contacting surface of the main diaper, capable of absorbing moisture and retaining loose excrement. The insert strip includes moisture proof bottom layer with extensions, which may be manipulated to prevent lateral overflow of moisture and excrement prior to and during removal of the soiled insert strip from the main diaper. The main diaper is such that it can be used without the insert and it also includes means to cover wastes therein while being removed from the body. Due to the small size of the insert, the liquid discharged by the baby tends to overwhelm the liquid capturing capacity of the insert. The plastic flaps provided occupy the area surrounding the small insert and do not provide moisture absorption capability. Their function is restricted to wrapping the removed insert. The insert does not contain moisture absorption super-absorbers. It has limited fluid absorption capability, with the result that the underlying diaper is frequently soiled. Accordingly, removal of the insert does not guarantee a fresh diaper underneath.

U.S. Pat. No. 4,838,885 to Bernardin discloses form-fitting self-adjusting disposable garment with a multilayered absorbent. This anatomically form-fitting, self-adjusting disposable garment has a stretchable outer cover. It provides fixed position fasteners and a multilayered absorbent structure. The multilayered absorbent structure has a liquid permeable body-side liner, a liquid impermeable barrier and an absorbent composite disposed between the liner and the barrier. The absorbent composite comprises a uniform composition of fluff or a mixture of a hydrogel and absorbent material. It may alternatively comprise a first and second layer of absorbent materials differing in densities or differing by pore sizes. The absorbent composite can further comprise a mixture of a hydrogel and a filler material, which may be a hydrophilic or hydrophobic material treated with a surfactant. The absorbent composite is not a diaper. Rather, it comprises an insert positioned within a disposable garment. The multilayered absorbent material is a single element with a liquid permeable covering on the body contacting side and a liquid impermeable barrier layer on the garment contacting side.

U.S. Pat. No. 4,892,598 to Stevens, et al. discloses a method of integrating an absorbent insert into an elastomeric outer cover of a diaper garment. This method integrates a fluid-absorbing component into a holding component of an anatomically form-fitting, generally self-adjusting absorbent garment. An elastomeric outer cover is provided for holding a relatively inelastic absorbent insert in selected bodily registration for absorbing and containing bodily fluids. A slidable hem retaining arrangement connects the insert to the outer cover. This arrangement includes cooperating fasteners that engage with one another through a plurality of fenestrations, allowing unrestricted elongation or retraction of the outer cover relative to the insert. The fasteners are releasably engageable with one another to allow removal and replacement of the insert when soiled. Alternatively, ultrasonic bonds may be used instead of refastenable closures, where a single-use disposable garment is produced. The elastomeric outer cover receives the fluid absorbing component. The diaper garment does not contain multiple diapers. It must be physically removed to replace the absorbent component.

U.S. Pat. No. 5,217,447 to Gagnon discloses a diaper system with detachable linings. This diaper assembly includes a reusable over-garment having opposite side edges and two opposite ends and inner and outer surfaces. An absorbent liner is adapted for positioning on the inner surface side of the over-garment. This liner also has opposite ends and inner and outer surfaces. There is a separate, disposable non-absorbent inner sheet adapted to cover the inner surface of the liner. Snap fasteners are provided for detachably connecting the opposite ends of both the liner and the inner sheet to respective opposite ends of the garment to enhance stability. A moisture proof sheet is disposed on the inner surface of the over-garment and this sheet has elasticized side edges. The replaceable liner is a single absorber positioned within the over-garment. The over-garment has to be first removed to replace the lining. The lining has no barrier on the side that contacts the outer-garment and, as a result, moisture proof sheet are utilized to prevent soiling of the over-garment. If the liner absorption capability is completely exhausted, the over-garment will become soiled.

U.S. Pat. No. 5,342,340 to Kichefski, et al. a discloses reusable diaper. This reusable leakproof diaper is said to be as convenient in use as a disposable diaper. It includes a one-or-more layered absorbent rectangular liner attached by strips of liquid impervious material to a liquid impervious outer shell. A closure system, such as snap fasteners, single looped closures, buttons, or hooks is mounted on the outer shell. The sides of the outer shell include elastic strips along the portion of the shell that forms a leg opening when the diaper is in use. The unique design for attaching the inner absorbent liner to the liquid impervious outer shell provides the diaper with improved resistance to leakage. This diaper is appointed for control of incontinence; and is not a baby diaper. The multiple absorbent layers are juxtaposed together. They are not individually removed to expose a fresh unsoiled liner.

U.S. Pat. No. 5,720,738 to Clark discloses an edge-protected, layered, absorbent product. This multilayered absorbent feminine hygiene product, which is configured for releasable attachment to a user's garment, has a plurality of absorbent pads. Each of the absorbent pads has an absorbent layer to contain absorbed fluid and a barrier layer to prevent absorbed fluid from leaking completely through the individual pad. The pads are releasably attached along at least a portion of their lateral edges with a protective material. The protective material protects unexposed absorbent pad layers from soiling by fluid runoff from the exposed pad layer. It contributes to the attachment strength between the layers during use. This product is a feminine hygiene product and is not a baby diaper. The plurality of pads used merely provide additional protection. Removal of the topmost soiled pad does not expose an unsoiled pad.

U.S. Pat. No. 5,725,518 to Coates discloses a reusable diaper having a gusseted pad insert. This reusable infant or adult diaper comprises a fluid absorbent pad on the inner surface of a waterproof, hourglass-shaped, diaper shell. A pair of fastener tabs extends from the rear corners of the diaper shell carrying filamentary hook fastener material. Slightly larger strips of filamentary loop material on the inner surface of the diaper shell cover the fastener tabs during washing to protect the filamentary hook material from buildup of lint. Each fastener tab and its cover, assembled to the diaper shell by a single continuous line of stitching and turned to the inside of the diaper, present a finished edge at a corner of the diaper shell. The diaper is fitted to the infant or adult by wrapping the shell around the pelvic region and coupling the fastener tabs to a pair of strips carrying filamentary loop material and arranged in a V-pattern on the front of the diaper. Several different mechanisms fasten the shell and absorbent material to the body of the wearer. Absorbent material may be sewn into the shell or be floating in the shell between the leg holes of the diaper. The absorbent material forms a single element which, when soiled, must be discarded. No means are provided to expose the soiled absorbent pad, or to pull it away to expose a fresh absorbent pad.

U.S. Pat. No. 6,114,597 to Romare discloses an absorbent product for receiving body fluids. This absorbent product, such as a sanitary napkin, a panty liner, an incontinence protector, or the like, is arranged in the crotch region of a user in order to collect and absorb discharged body fluids. Means are provided for fastening the diaper inside a pair of underpants. The product has a principally elongated shape with a longitudinal centerline and a transverse centerline. The upper part of the product faces towards the user and a lower part of the product faces away from the user. The upper and lower parts are mutually joined, so that each has a front part facing forwardly towards the abdomen of a user while the rear part faces rearwardly towards the behind of the user. The upper part and the lower part further each have a front transverse edge and a rear transverse edge, as well as two longitudinal side edges extending between the two transverse edges. The upper part and the lower part are mutually joined only at the acquisition zone of the product, which is the region of the product which is intended to first be wetted by body fluid. The upper part surrounding the entire periphery of the acquisition zone is free from connections to the lower part. This product is not a diaper; the body fluid absorption member is an elongated body. The lower part of the absorber has a barrier, and is removably attached to inside of underpants. The absorber cannot be removed and new one reattached without first removing the underpants.

U.S. Pat. No. 6,193,702 to Spencer discloses, in combination, a reusable undergarment and a disposable absorbent article. This reusable undergarment has the shape of a panty of lightweight stretchable fabric. It has a seat of fluid resistant material where one or more female receiving grooves are stitched or depressed at a standard spacing that runs transverse to the longitudinal axis of the reusable undergarment seat. A disposable absorbent article of pre determined material is provided with one or more male insert ridges at a standard spacing, which corresponds to that of the female receiving grooves in the seat of the reusable undergarment. The disposable absorbent article is replaced on the reusable undergarment. The undergarment of the '702 disclosure is not a baby diaper. Moreover, the absorbent article has to be entirely replaced. There is no disclosure that involves pulling away a soiled baby diaper to expose a fresh baby diaper.

U.S. Pat. No. 6,336,923 to Fujioka, et al. discloses disposable diapers. This disposable diaper has front and a rear bodies permanently welded together at a crotch zone along a welding line that convexly curves upwardly. Fasteners are formed along side edges of one of the front and rear bodies to enable the bodies to be releasably attached together to form the basic structure of the diaper. An auxiliary liquid absorbent panel is permanently attached to float above the convexly curved welding line of the crotch zone for greater absorbency. This disposable diaper has portions that fit around the legs and waist of the user. The crotch portion has a welded absorbent pad, which is not removed when soiled to expose a fresh pad.

U.S. Pat. No. 7,090,665 to Ohashi, et al. discloses a disposable diaper. This disposable diaper includes an air permeable cover member and a body fluid absorbent member attached to an inner side of the cover member. The absorbent member is composed of a liquid-pervious topsheet, an air permeable backsheet and an absorbent core member disposed therebetween. The absorbent member is formed on a side adjacent the backsheet with at least one first groove concaved in a direction from the backsheet toward the topsheet. This diaper must be opened outwardly and discarded. There is no means provided to quickly remove a soiled diaper while exposing a fresh diaper.

Absorbent composites suitable for use in disposable absorbent garments such as diapers, adult incontinent products, and the like, are known. Such absorbent composites are described, for example, in U.S. Pat. No. 4,699,619 to Bernardin; U.S. Pat. No. 4,798,603 to Meyer et al.; U.S. Pat. No. 4,834,735 to Alemany et al.; U.S. Pat. No. 5,147,343 to Kellenberger; and U.S. Pat. No. 5,149,335 to Kellenberger et al.

Generally, such absorbent composites comprise a means of containing a high-absorbency material and a high-absorbency material. Suitable means for containing the high-absorbency material include fibrous matrixes, such as those formed from air-laid cellulosic fibers or a co-form material comprising cellulosic fibers and meltblown polyolefin fibers. A wide variety of high-absorbency materials (also known as superabsorbent materials) are known to those skilled in the art. See, for example, U.S. Pat. No. 4,076,663 to Masuda et al.; U.S. Pat. No. 4,286,082 to Tsubakimoto et al.; U.S. Pat. No. 4,062,817 to Westerman; and U.S. Pat. No. 4,340,706 to Obayashi et al.

U.S. Pat. No. 4,333,461 to Muller discloses borated polysaccharide absorbents and absorbent products. Guar gum as an exemplification of cis-1,2-diol polysaccharides is first hydrated then thickened by cross-linking with borax and finally dried to powder in flake form, preferably by freeze drying. The resulting particles can absorb up to 100 times their weight or more of aqueous fluids such as urine. Absorbent articles, such as disposable diapers, bandages, and the like are formed with the borax-cross-linked guar gum as absorbent. In a preferred diaper the dry absorbent particles of the borax cross-liked guar gum are placed in the cells of a cellular or bubble-type substrate. The resultant material forms a superabsorbing polymer. No disclosure is contained within the '461 patent concerning use of such a polymer in a baby's double diaper system.

U.S. Pat. No. 4,360,021 to Stima discloses an absorbent article. This absorbent article comprises a cover sheet and a backing sheet. The cover and backing sheets are attached in areas without the use of water-insoluble adhesives to form pockets in which a fluid absorbent material is stored. The absorbent article is formed by depositing portions of the fluid absorbent material on the backing sheet, placing the cover sheet over the absorbent material and the backing sheet, and pressing the cover sheet towards the exposed parts of the backing sheet to cause bonding of the fibers in each sheet and attaching the cover sheet to the backing sheet to form pockets in which the absorbent material is stored. The absorbent material comprises a mixture of (a) a derivatized or underivatized cis-1,2-diol polysaccharide, boric acid and an alkali material or (b) a borate cross-linked guar gum and alkali. This absorbent article is not indicated to be incorporated in a baby diaper.

Notwithstanding the efforts of prior art workers to provide diapers for babies that are easily changeable, there remains a need in the art for a diaper system wherein two diapers are placed one above the other and bonded together with a releasable adhesive, so that the inner soiled diaper may be easily pulled away and discarded to reveal an outer diaper that provides a fresh urine absorbing diaper surface that has not been contaminated by the inner soiled diaper. A diaper with this capability would be extremely useful during traveling or shopping situations, where changing a baby takes substantial time and effort and facilities that accommodate a full diaper change and cleaning operation are limited.

SUMMARY OF THE INVENTION

The present invention provides a diaper system wherein two diapers are placed one above the other and bonded together with a releasable adhesive, so that the inner soiled diaper may be easily pulled away and discarded. Advantageously, with the present diaper system, removal of the inner soiled diaper reveals an outer diaper that provides a fresh urine absorbing diaper surface, which has not been contaminated by the inner soiled diaper. The double duty diaper system of this invention is especially suitable for use when traveling or in shopping situations. Diapers are changed with much less effort and diaper changing times are substantially reduced. Changing of diapers is readily effected on the fly without need for facilities that accommodate a full diaper change and cleaning operation.

Generally stated, the double duty diaper system comprises at least two similarly sized diapers. An inner diaper and an outer diaper are adhesively attached to each other by the edge flap portion of the inner diaper. Each of the inner and outer diapers comprises a super-absorber, such as borated polysaccharide absorbents in fibrous matrix, encased in a liquid permeable net, preferably a polyethylene, polypropylene, nylon or polyester porous net, at the skin contact area. In addition, each of the inner and outer diapers has a liquid impervious polymeric layer on a non-skin contacting surface that is distal from the net. The soiled inner diaper can be easily peeled away by pulling at the edge flap. With this pulling action, the adhesive bond becomes detached and causes the soiled inner diaper to be easily removed from the outer diaper. A fresh liquid absorbing surface is thereby exposed, enabling uncontaminated contact between the outer diaper and the baby's skin. During this peel away of the inner diaper, the unsoiled portion of the inner diaper may be used to wipe away any fecal matter present on the baby's skin. The inner diaper may be folded over and secured using the adhesive flap edge; and discarded as a closed, compact package.

The inner and outer diapers are packaged together and marketed as one unit. The inner diaper has an adhesive coated edge over-flap, which is folded over to the outer diaper's polymeric liquid impermeable sheet, securing the outer diaper to the inner diaper. Both inner and outer diapers have a pair of waist attachment tabs that are used to secure the diaper package around the waist of a baby. The liquid permeable net of the inner and outer diaper is typically made from a net woven or non-woven polyethylene, polypropylene fibers, nylon, polyester or other suitable materials. The liquid impermeable polymeric sheet is made from a film of polyethylene, polypropylene, polyolefin, or polyvinylchloride or other suitable polymeric material. A super-absorber such as borated polysaccharide in a fibrous matrix absorber is contained between the liquid permeable net and the liquid impervious polymeric sheet. It is entirely contained or sealed by fusing or bonding of the net to the polymeric sheet around the edges of the super-absorber. The fibrous matrix of the super-absorber may include cotton, cellulose, melt blown polyolefin fibers or other suitable fibers. Even though the inner and outer diapers are similarly sized, the sealed side edge of the inner diaper is extended to create an edge flap typically of the same material as the liquid impervious polymeric sheet. This edge flap has an upper surface along the direction where the super-absorber is placed, and a lower surface that is away from the super-absorber. The lower surface of the edge flap of the inner diaper is coated with the adhesive layer. This adhesive layer is similar to that used in stickie notes such as those marketed by 3M under the trademark Post It™. It is therefore capable of being easily attached to the polymeric sheet of the outer diaper when the polymeric flap is folded over the outer diaper, and thereafter released, when necessary. When the edge flap of the inner diaper is peeled away, no adhesive is left behind on the liquid impermeable polymeric sheet of the outer diaper. With this diaper construction, skin irritation of the baby is substantially prevented. The inner diaper, with the attached outer diaper, is secured to the waist of a baby using waist tabs associated with the inner diaper.

In operation, when a parent or guardian perceives that the inner diaper is soiled, the waist attachment tabs of the inner diaper are released. The inner diaper is peeled away from the outer diaper by releasing the adhesive attachment at the edge flaps of the inner diaper, and the outer diaper is allowed to dangle. The baby's bottom is then wiped with the unsoiled portion of the inner diaper. The used, soiled, inner diaper is completely released from its contact with the outer diaper, and the adhesive coated edge flap of the inner diaper is used to fold and contain any fecal residue within the soiled inner diaper. The outer diaper waist retaining tabs are used to attach the outer diaper to the baby, exposing the fresh unsoiled outer diaper to contact baby's skin.

During use of the double diaper all soiling first occurs solely on the inner diaper. Soiling of the outer diaper is prevented due to the presence of a plurality of structural embodiments contained by the double duty diaper system. First, the inner diaper and the outer diaper are similarly sized, with the result that urine cannot pass from the inner diaper to the outer diaper. Secondly, the edge-flap of the inner diaper that folds over the outer diaper and attaches to the liquid impervious polymeric sheet also prevents the migration of the urine from the inner diaper to the outer diaper. Since both the inner diaper and outer diaper contain super-absorbers, their ability to absorb liquids is typically 50 to 100 times the volume of the super-absorbers. Advantageously, the diaper construction and use of the super-absorbers substantially prevents any of the urine collected in the inner diaper from reaching the outer diaper.

BRIEF DESCRIPTION OF THE DRAWINGS

The invention will be more fully understood and further advantages will become apparent when reference is had to the following detailed description of the preferred embodiments of the invention and the accompanying drawings, in which.

DETAILED DESCRIPTION OF THE INVENTION

The present invention provides similarly sized inner and outer diapers that are attached to each other by an adhesive coated edge flap that is provided around the edges of the inner diaper. Both the inner and diapers have a top surface of liquid permeable net preferably made from woven or non woven polyethylene, polypropylene, nylon, polyester or other suitable material. The under side of both the inner and the outer diaper is provided with a liquid impervious polymeric sheet, which prevents seepage of urine. In between the liquid permeable net and the liquid impervious plastic sheet is disposed a super-absorber that absorbs approximately 50 to 100 times the weight of liquid, as compared to the weight of the super-absorber. The super-absorber may advantageously be combined with a fibrous matrix of cotton, cellulose or melt blown polyolefin fibers. The liquid permeable net and liquid impervious plastic are bonded at the edges of the super-absorber, totally encasing the super-absorber. The inner diaper has an edge flap provided along this bond seam, and this edge flap is coated with an adhesive facing the polymer underside. Thus the outer diaper may be placed below the inner diaper with their corresponding liquid impervious polymer facing upwards and the edge flap of the inner diaper folded over the edges of the outer diaper to secure both diapers as a single package. This diaper package is manufactured and marketed with the inner and outer diapers attached. The user simply pulls out the waist retaining tabs of the inner diaper and attaches the diaper package to the baby's waist. As the baby uses the diaper, only the inner diaper gets soiled. When the parent decides to remove the inner diaper, the waist tabs of the inner diaper are undone and the inner diaper and outer diaper are separated by undoing the edge flap adhesive attachment. Since the adhesive is only present on the edge flap of the inner diaper, there is no adhesive transfer to the liquid impervious plastic surface of the outer diaper thereby preventing any skin irritation of the baby. The unsoiled portion of the inner diaper is used to wipe off the bottom of the baby. The soiled inner diaper is then folded over and the adhesive in the edge flap is used to secure the contents of the soiled diaper as a compact package ready for disposal. The waist tabs of the outer diaper are used to attach the clean outer diaper to the waist of the baby.

This double diaper is particularly advantageous in that the parent does not have to carry multiple diapers and look for washcloth to wipe the baby's bottom. The clean outer diaper is always present and is very convenient during travel, shopping, and the like. The soiled inner diaper is also neatly folded and secured for easy disposal.

FIGS. 1-4 depict the double diaper package of the present invention. The numbering sequence is preserved in these figures for clarity. The outer diaper has a liquid permeable net 11a and a liquid impermeable polymeric sheet 11b containing the super-absorber therebetween. Similarly, the inner diaper has liquid permeable net 21a and a liquid impermeable polymeric sheet 21b containing the super-absorber therebetween. The outer diaper has a pair of waist-securing tabs 13 and the inner diaper has a pair of waist-securing tabs 23. The inner diaper has edge flap 22 for attaching the inner and outer diapers. It should be understood that the outer and inner diapers, respectively, are said to be similarly sized as described herein above and below. Though the inner 21 and outer 11 diapers are similarly sized (but for manufacturing intolerances and the like), the sealed side edge of the inner diaper is extended to create edge flap 22, typically composed of the same material as the liquid impervious polymeric sheet 11b, 21b. Thus this extended side edge of the inner diaper 21 (i.e. edge flap 22) results in inner diaper 21 being slightly larger (as per edge flap 22) so as to extend beyond the outer diaper 11. See FIGS. 1, 3 and 4 for illustrative purposes.

Figure 1:
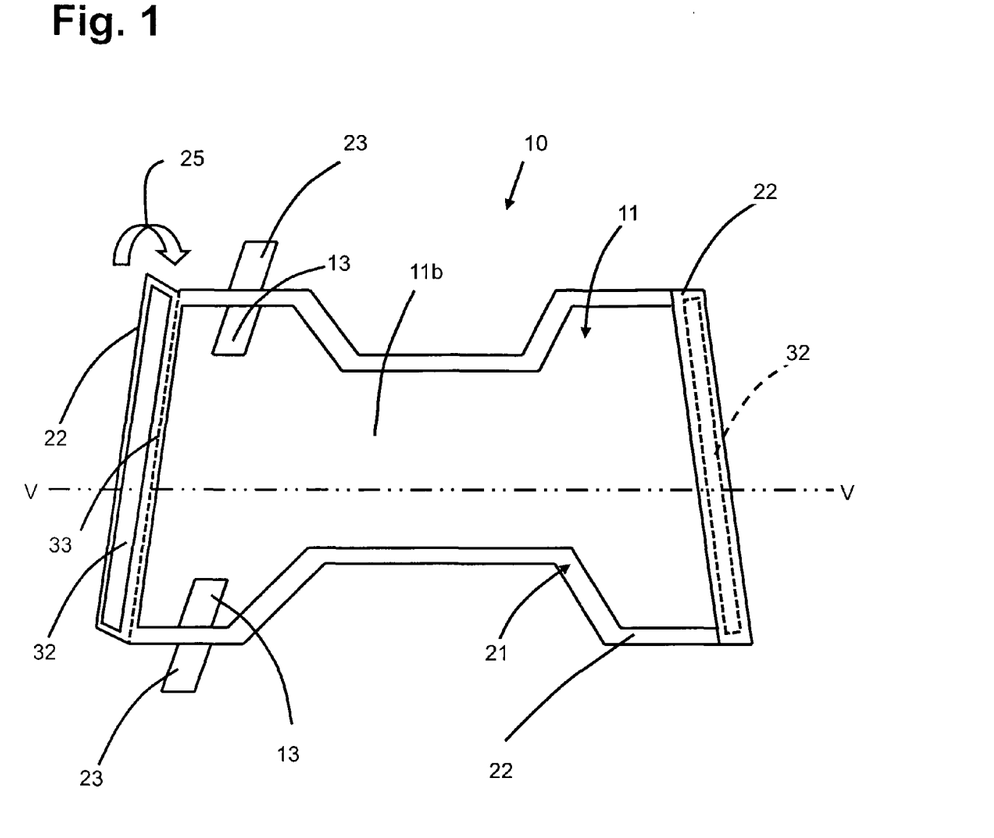
FIG. 1 is a perspective view of the double diaper package of the present invention facing the liquid impermeable plastic sheet of the outer diaper, showing the inner and outer diapers attached to each other by folding the adhesive coated edge flap of the inner diaper over the liquid impermeable polymeric sheet of the outer diaper, which is visible in this view.

FIG. 1 illustrates generally at 10 the double diaper package showing the outer diaper at 11 and the inner diaper at 21. Outer diaper 11 includes a liquid impermeable polymeric sheet 11b. The outer diaper 11 has a liquid permeable net 11a (shown at FIG. 3 and FIG. 4) designed to contact the skin. The outer diaper 11 has a pair of tabs 13 to attach the outer diaper 11 to the waist of the baby. The inner diaper 21 is similarly sized to the outer diaper 11 (shown generally in FIGS. 3 and 4). The inner diaper 21 is disposed directly below the outer diaper 11 and therefore is not visible in this figure other than by way of edge flap 22 and tabs 23 of the inner diaper 21. The edge flap 22 and tabs 23 of the inner diaper 21, which has an adhesive coating 32 (shown in phantom wherein edge flap 22 is in the closed configuration as on the far right of outer diaper 11), is attached to the impervious polymeric sheet 11b of the outer diaper 11. Block arrow 25 depicts the manner in which the edge flap 22 is secured. Edge flap 22 is shown in the open condition on the far left of the figure as indicated by a fold line 33, wherein adhesive coating 32 is shown as no longer bonded to liquid impermeable polymeric sheet 11b of outer diaper 11. Conversely edge flap 22 is shown in the closed condition on the far right of the figure, wherein adhesive coating 32 (herein shown as dashed lines as under closed edge flap 22) is bonded to liquid impermeable polymeric sheet 11b of outer diaper 11.

Figure 2:
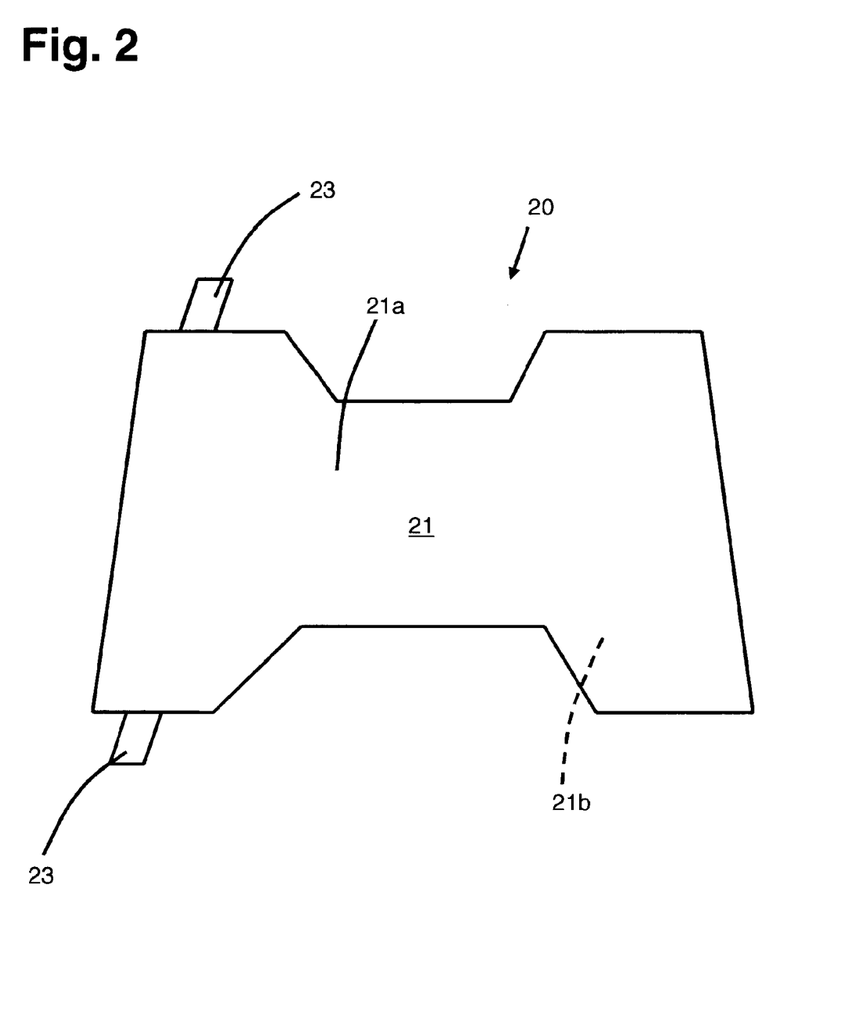
FIG. 2 is a perspective view of the double diaper package of the present invention facing the liquid permeable net of the inner diaper (the details of the net omitted for clarity), showing the inner and outer diaper attached to each other and the inner diaper waist-securing tabs, which are visible in this view.

FIG. 2 illustrates generally at 20 the double diaper package, facing the liquid permeable net 21a of the inner diaper 21 (the details of the net omitted for clarity), depicting the double diaper package of FIG. 1 that is flipped over. The liquid impervious polymer surface 21b (shown at FIG. 3), shown in phantom herein to depict same is on the underside of this view, of the inner diaper 21 is directly below the liquid permeable net 21a (save for the super-absorber located therebetween, see FIG. 4). Directly below the inner diaper 21 is the outer diaper 11, which is not visible in this figure. A pair of waist-securing tabs 23 of the inner diaper 21 are shown by the figure in an opened out condition, ready to be attached to the waist of the baby. The inner diaper 21 is attached to the outer diaper 11 by a folded edge flap 22, which is not visible in this view.

Figure 3:
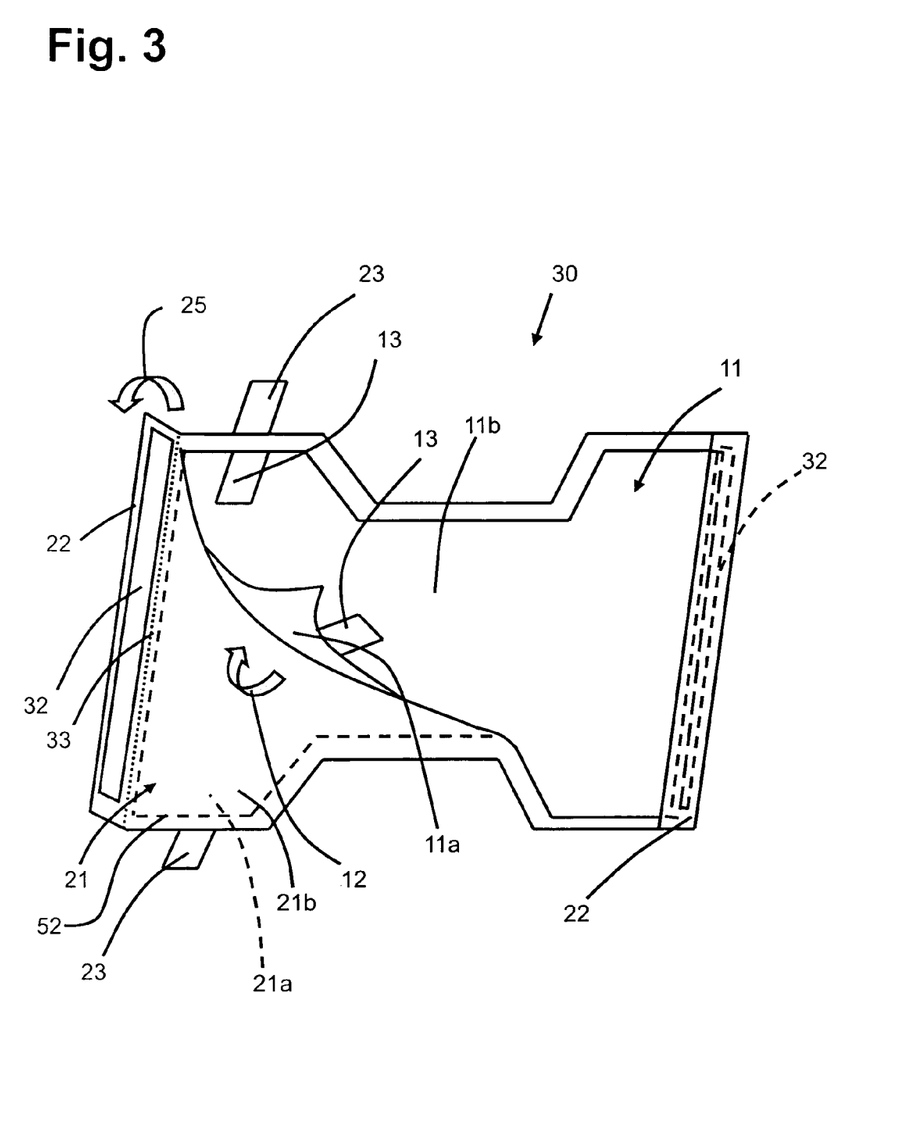
FIG. 3 is a perspective view of the double diaper package of the present invention, showing the inner diaper being removed from the outer diaper.

FIG. 3 illustrates generally at 30 the condition of the double diaper package at a time when the soiled inner diaper 21 is being separated and removed from the outer diaper 11. First, the waist contacting tabs 23 of the inner diaper 21 are unfastened. Next, the adhesive 32 coated edge flap 22 of the inner diaper 21 is opened out, as shown by the block arrow 25. The perspective view of FIG. 3 faces the inner diaper 21 and outer diaper 11 from the liquid impermeable sides 11b and 21b of both outer and inner diapers, 11 and 21, respectively. The liquid permeable net 21a side shown in phantom lines to indicate same is on the underside of the figure) of the inner diaper 21 is below liquid impervious polymer surface 21b, with a super-absorber layer therebetwen (see FIG. 4). The baby's bottom will be directly below liquid permeable net 21a (shown at FIG. 2) of the inner diaper 21. The outer diaper 11 is peeled away from the inner diaper 21 as shown by block arrow 12. The inner diaper 21 is pulled out and an unsoiled portion of the inner diaper 21 is used to wipe the bottom of the baby. The inner diaper 21 is folded and the adhesive 32 coated flap 22 is used secure the folded inner diaper 21, creating a compact package that is ready for disposal. The outer diaper 11, which has a clean liquid permeable net 11a (the details of the net omitted for clarity), is now attached to the waist of the baby, using pair of tabs 13. Edge flap 22 is shown in the open condition on the far left of the figure as indicated by a fold line 33, wherein adhesive coating 32 is shown as no longer bonded to liquid impermeable polymeric sheet 11b of outer diaper 11. Conversely, edge flap 22 is shown in the closed condition on the far right of the figure, wherein adhesive coating 32 (herein shown as dashed lines as under closed edge flap 22) is bonded to liquid impermeable polymeric sheet 11b of outer diaper 11.

Figure 4:
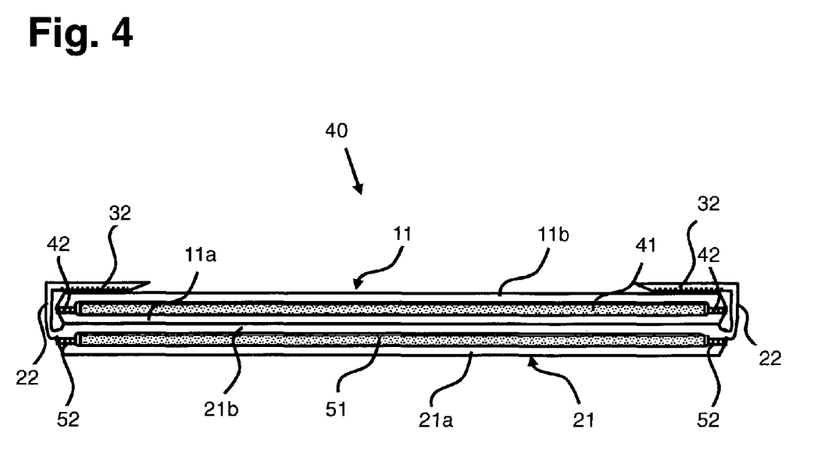
FIG. 4 illustrates a cross-sectional view of the double diaper package shown in FIG. 1 taken along line V-V, showing a cross-sectional side view of the inner and outer diapers attached to each other by folding the adhesive coated edge flap of the inner diaper over the liquid impermeable polymeric sheet of the outer diaper.

FIG. 4 illustrates a cross-sectional view of the double diaper package 10 shown in FIG. 1 taken along line V-V, shown generally at 40. The cross-sectional side view of the double diaper package shows the inner and outer diapers, 21 and 11, respectively, attached to each other by folding the adhesive 32 coated edge flap 22 of the inner diaper 21 over the liquid impermeable polymeric sheet 11b of the outer diaper 11. Inner and outer diapers, 21 and 11, are each constructed having a liquid permeable net 21a and 11a, super-absorber 51 and 41, polymeric sheet 21b and 11b, bonded by way of edge bond 52 and 42. Edge flap 22 of inner diaper 21 is shown in a folded condition with adhesive edge 32 bonded with polymeric sheet 11b of outer diaper 11. Inner diaper 21 comprises an adhesive 32 coated edge flap 22 integrated within the impermeable polymeric sheet 21b, in a manner so that the edge flap 22 extends outwardly, beyond the edge bond 52 of inner diaper 21 and adheres to polymeric sheet 11b of outer diaper 11 until separation is sought.

Since the inner diaper and the outer diaper are similarly sized, there is no possibility for the baby's urine to soil the outer diaper. Moreover, the inner diaper contains a super-absorber that can absorb approximately 50 to 100 times its own weight of liquid. With this arrangement, there is adequate liquid absorption capacity present within the inner diaper to prevent migration of liquid to the outer diaper. The folded over edges of the inner diaper cover the liquid impervious portion of the outer diaper, further serving to substantially prevent entry of urine into the outer diaper. As a consequence, the liquid permeable net of the outer diaper is kept substantially clean and fresh.

The double diaper package comprises the following features in combination:

1) similarly sized inner and outer diapers;
2) the inner diaper having a liquid permeable net sheet, and a liquid impervious polymer sheet that is bonded at the edges and surrounds a super-absorber contained therebetween;
3) the inner diaper having an extension of the edge flap with an adhesive coating on the side of the impervious polymer sheet opposed to the super-absorber side;
4) said outer diaper having a liquid permeable net sheet, a liquid impervious polymer sheet bonded at edges surrounding a super-absorber contained therebetween;
5) said inner diaper being placed above the outer diaper with the liquid permeable net of both inner and outer diapers facing the same direction, and the adhesive coated edge flaps of the inner diaper being folded over the outer diaper, thereby attaching the outer diaper to the inner diaper and forming a double diaper package;
6) waist tabs of said inner diaper being opened and said double diaper package being attached to a waist of a baby;
7) a parent removing said waist tabs of the inner diaper, separating the soiled inner diaper from the clean outer diaper at the adhesive attachment of said edge flap, wiping the baby's bottom with an the unsoiled portion of inner diaper and discarding the soiled inner diaper, and
8) the parent attaching waist tabs of the outer diaper to the waist of the baby, whereby the unsoiled outer diaper is secured to the baby's waist while the soiled inner diaper is neatly packaged by an adhesive coated edge flap and discarded.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A double diaper package comprising:
   a. similarly sized inner diapers and outer diaper, each provided with a pair of waist-securing tabs;
   b. said similar sized inner and outer diapers each comprising a liquid permeable net and a liquid impermeable polymeric sheet edge bonded to each other so as to surround and encase a super-absorber, the polymeric sheet having one side adjacent the super-absorber and a side remote from the super-absorber;
   c. said inner diaper further comprising an edge flap defined by an extension of the impermeable polymeric sheet which extends beyond and outward from the edge bond and an adhesive coated on the remote side of the impermeable sheet defining the extension;
   d. said inner diaper located coextensively over the similarly sized outer diaper with the impermeable sheet of the inner diaper facing the permeable sheet of the outer diaper and attached to said outer diaper with the adhesive coated edge flap folded around the edge bond and over the liquid polymeric sheet of said outer diaper;
   e. said double diaper package being adapted to be attached to a waist of a baby using said waist-securing tabs of the inner diaper;
   f. said waist-securing tabs of inner diaper being adapted for removal when said inner diaper is soiled;
   g. said adhesive attachment of the edge flap of the inner diaper to the outer diaper adapted to be removed when the inner diaper is soiled, thereby freeing said outer diaper and facilitate discarding of said soiled inner diaper; and h. said waist-securing tabs of the outer diaper being adapted to be attached around the waist of said baby after removal of the soiled inner diaper, whereby the fresh unsoiled outer diaper is securable to the baby's waist while the soiled inner diaper is discarded.

2. The double diaper package as recited by claim 1, wherein said double diaper is marketed with said inner and outer diaper attached by said folded edge flap.

3. The double diaper package as recited by claim 1, wherein said liquid permeable net is made from woven or non-woven polymer fibers.

4. The double diaper package as recited by claim 3, wherein said polymer fibers are selected from a group consisting of polyethylene fibers, polypropylene fibers, nylon fibers and polyester fibers.

5. The double diaper package as recited by claim 1, wherein said liquid impermeable polymeric sheet is selected from the group consisting of polyethylene sheet, polypropylene sheet, polyolefin sheet and polyvinylchloride sheet.

6. The double diaper package as recited by claim 5, wherein said super-absorber contains borated polysaccharide together with a fibrous matrix of cotton, cellulose or melt blown polyolefin fibers.

7. The double diaper package as recited by claim 1, wherein said inner diaper upon removal is usable to wipe said baby's bottom using unsoiled portions of the soiled inner diaper.

8. The double diaper package as recited by claim 1, wherein said soiled inner diaper is wrappable and securable in wrapped form using said adhesive coated edge flap to form a compact package for easy disposal.

* * * * *